United States Patent [19]

Facker et al.

[11] Patent Number: 5,530,165
[45] Date of Patent: Jun. 25, 1996

[54] PRODUCTION OF A HIGH PURITY ETHER PRODUCT

[75] Inventors: Michael L. Facker; Gary R. Patton; Ronald E. Miranda, all of Bartlesville, Okla.

[73] Assignee: Phillips Petroleum Company, Bartlesville, Okla.

[21] Appl. No.: 322,896

[22] Filed: Oct. 13, 1994

[51] Int. Cl.$^6$ .................................................. C07C 41/00
[52] U.S. Cl. ............................................................. 568/697
[58] Field of Search ............................................. 568/697

[56] References Cited

U.S. PATENT DOCUMENTS

| | | | |
|---|---|---|---|
| 4,198,530 | 4/1980 | Wentzheimer et al. | 568/697 |
| 4,329,516 | 5/1982 | Al-Muddarris | 568/697 |
| 4,371,718 | 2/1983 | Hutson, Jr. | 568/697 |
| 4,906,788 | 3/1990 | Scott et al. | 568/697 |
| 5,143,888 | 9/1992 | Olbrich | 502/329 |
| 5,237,109 | 8/1993 | Patton et al. | 568/697 |
| 5,237,115 | 8/1993 | Makovec et al. | 585/314 |
| 5,313,004 | 5/1994 | Harandi | 568/697 |

FOREIGN PATENT DOCUMENTS 2054990  5/1992  Canada.

*Primary Examiner*—Paul J. Killos
*Attorney, Agent, or Firm*—Charles W. Stewart

[57] ABSTRACT

A process for producing a high purity ether product. This process includes utilizing an additive stream, which preferably contains isobutane, to alter compositions of the overhead and bottoms products of an etherification effluent fractionator so that the alcohol concentration in the overhead product is less than that of the azeotropic composition.

12 Claims, 1 Drawing Sheet

PRODUCTION OF A HIGH PURITY ETHER PRODUCT

This invention relates to the manufacture of a high purity ether product.

Ether compounds are well known as blending components for gasoline. In certain etherification processes, ether compounds are produced by reacting within a reaction zone an isoolefin with an alcohol to produce an ether compound. The reaction product from the etherification reaction zone undergoes a separation to remove the ether product from the non-reactive and unreacted components of the etherification reaction zone feed. In situations where the isobutylene concentration of the etherification reaction zone feed is significant, large quantities of the alcohol reactant can pass through the reaction zone unreacted. Thus, the alcohol concentration in the etherification reactor effluent will be such that it becomes difficult to separate from the ether by fractionation. This difficulty in separation is due to the azeotropes that form between alcohols and paraffins.

Because of the limited availability of olefin feedstock for etherification processes, a dehydrogenation process can be used to dehydrogenate isoparaffins to form isoolefins suitable for use as a feedstock to etherification processes. The combining of a dehydrogenation process with an etherification process can impact the composition of the etherification process feed and its product streams. When these processes are used in combination with a fractionator for separating ether from the other components of the etherification process product stream, the compositions of the etherification process product stream will sometimes be such that a high purity ether product is unobtainable by straight fractionation.

It is thus an object of this invention to provide for the production of a high purity ether product containing a desired minimum concentration of alcohol.

Another object of this invention is to provide for a combination of processes that can be operated to give a high purity ether product, particularly one having a desired minimum concentration of alcohol.

One embodiment of the invention is a method for fractionating an etherification reaction zone product stream so as to provide a high purity ether product and an overhead product. A controlled amount of isobutane is mixed with the etherification reaction zone product stream to form a mixed stream. The mixed stream is fractionated into the high purity ether product and the overhead product. The controlled amount of isobutane mixed with the etherification reaction zone product stream is such as to permit the reduction of an alcohol concentration in the high purity ether product below a desired concentration.

Another embodiment of the invention includes passing a feed comprising isobutane to a dehydrogenation process system for dehydrogenating the isobutane in said feed and to thereby provide an isobutylene feed. The isobutylene feed is passed to an etherification process system for reacting the isobutylene of said isobutylene feed with an alcohol to thereby provide an etherification reaction zone product stream. The etherification reaction zone product stream is mixed with isobutane to form a mixed stream which is passed to a fractionator whereby the mixed stream is separated into a bottoms product comprising ether and an overhead product comprising isobutane and alcohol. The overhead product is mixed with the feed to the dehydrogenation process system.

Figure 1:
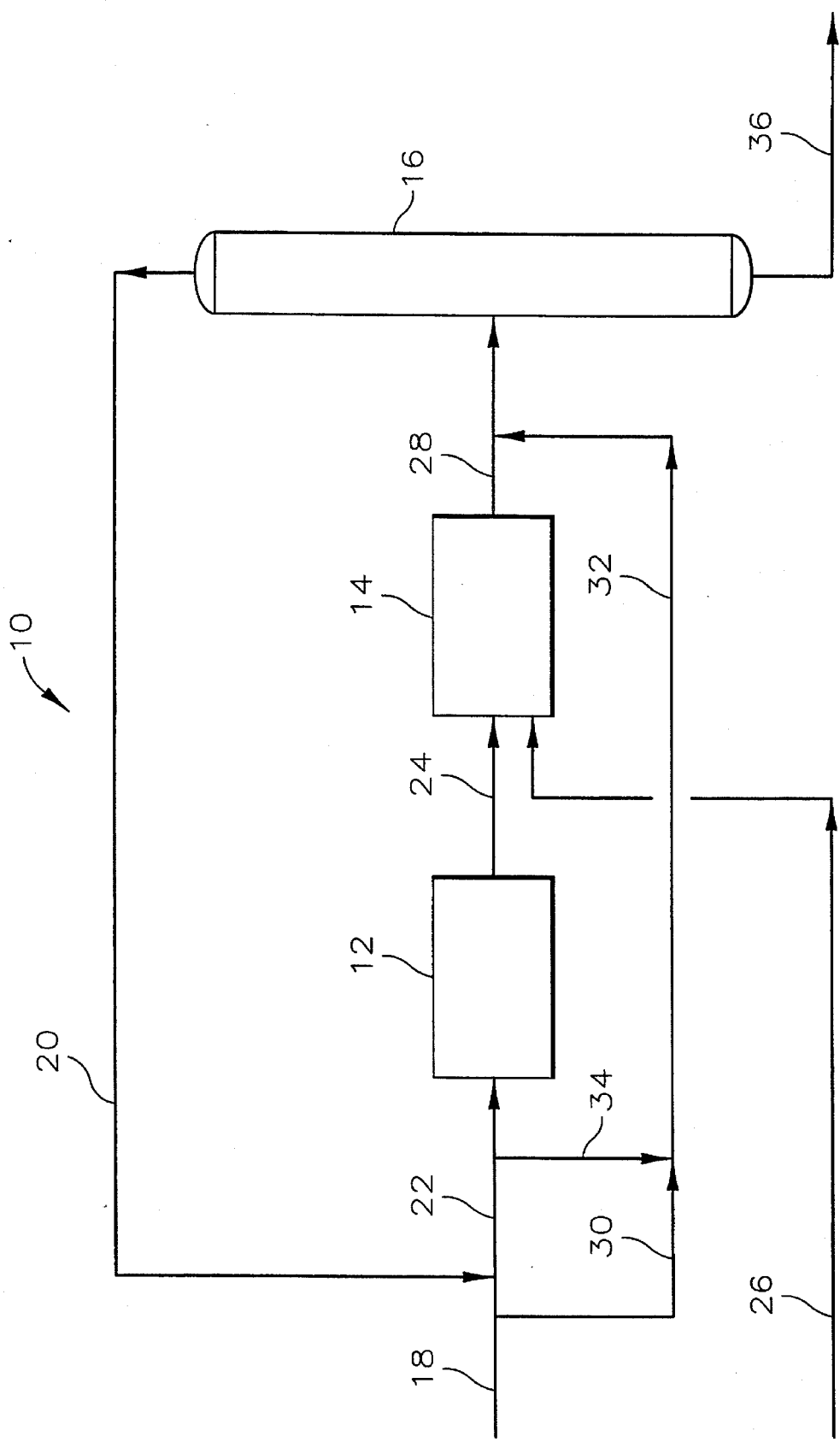
FIG. 1 provides schematic representation of the combination process which is one embodiment of the invention.

Other objects and advantages of the invention will be apparent from the detailed description of the invention and the appended claims.

The inventive process solves certain problems associated with the fractional separation of an etherification reaction zone product stream, particularly, when the etherification system is integrated with an overall combination of subprocesses which can include dehydrogenation and separation processes. Specifically, the presence of alcohol in an etherification reaction zone product stream often causes difficulty in separation due to the azeotropic composition formed with the hydrocarbons and ethers of the etherification reaction zone product stream. The amount of alcohol contained in the etherification reaction zone product stream is generally set by the concentration of isobutylene contained in the etherification reaction zone feed. As the concentration of isobutylene increases, the stoichiometric requirement of alcohol reactant correspondingly increases. Therefore, as the alcohol concentration in the etherification reaction zone feed increases, there is also a corresponding increase in the amount of alcohol contained in the etherification reaction zone product stream. The etherification reaction zone product stream is charged or fed to a fractionation column whereby it is separated into an overhead product containing alcohol and non-reactive or unreacted hydrocarbons and a bottoms product.

When the concentration of alcohol in the etherification reaction zone product stream exceeds a certain level, it becomes impossible to perform fractional separation of such stream so as to provide a bottoms product having an acceptably low concentration of alcohol or, alternatively, so as to provide an acceptably high purity ether product. A novel aspect of the present invention includes mixing a controlled amount of isobutane with the etherification reaction zone product stream to provide a mixed stream to be charged to the fractionator. The amount of isobutane mixed with the etherification reaction zone product stream is such as to be effective in altering the composition of either the overhead product or bottoms product, or both, so as to permit the reduction of the alcohol concentration in the bottoms product below a desired concentration.

Generally, for the instant invention, it is desired for the concentration of alcohol in the bottoms product of the fractionator to be less than about 1.5 mol percent, preferably, less than about 1.0 mol percent, most preferably, less than 0.5 mol percent. By mixing isobutane with the etherification reaction zone product stream, the percentage concentration of alcohol will be reduced and compositions of the overhead product and bottoms product are altered so that the alcohol content in the overhead product is below that of the azeotropic composition. Thus, the quantity of isobutane mixed with the etherification reaction product stream is set by the desired alcohol concentration in the bottoms product.

While the quantity of isobutane mixed with the etherification reaction product stream is set by the desired alcohol concentration in the bottoms product, the quantity of isobutane added per quantity of ether contained in the etherification reaction zone product stream can range upwardly to about 4 mols isobutane per mol ether (4:1), preferably, from about 3:1 to about 1:3 and, most preferably from 2:1 to 1:2.

In typical operations, the alcohol concentration in the etherification reaction zone product stream will be in the range of from about 1 to about 20 mol percent. It is desirable to mix an amount of isobutane with the etherification reactor product so as to give an alcohol concentration in the mixed stream that is less than about 5 mol percent. While the desired concentration of alcohol in the mixed stream is determined or set by the desired concentration of alcohol in the bottoms stream, the preferred concentration is less than about 4 mol percent and, most preferably, it is less than 3 mol percent.

One embodiment of this invention is an integrated combination of subprocesses that include etherification, dehydrogenation and fractionation. The combination uniquely provides for the processing of paraffin hydrocarbons so as to provide olefin feedstock for an etherification process and for the separation and reuse of reactants from an etherification reactor product stream. This integrated arrangement provides for a high purity ether product, particularly, an ether product having a minimum concentration of alcohol therein.

The dehydrogenation subprocess can be any dehydrogenation process which employs a dehydrogenation catalyst. This dehydrogenation subprocess is particularly suitable for use when the dehydrogenation catalyst comprises (1) a support selected from the group consisting of alumina, silica, magnesia, zirconia, alumina-silicates, Group II Aluminate spinels and mixtures of two or more thereof and (2) a catalytic amount of at least one Group VIII metal. (Groups of metals as referred to herein are the groups of metals as classified in the Periodic Table of the elements as set forth in Chemical Rubber Company's "Handbook of Chemistry and Physics", 45th Edition (1964), page B-2).

Any catalytically active amount of Group VIII metal can be employed in the steam active dehydrogenation catalysts. Generally the Group VIII metal is present in the catalyst in an amount in the range of about 0.01 to about 10 weight percent of the weight of the support, more often about 0.1 to about 5 weight percent.

Other suitable copromoter metals can also be employed in the dehydrogenation catalyst in conjunction with the Group VIII metal. A preferred type of such co-promoters are Group IVa metals selected from the group of lead, tin, and germanium. The Group IVa metal can exist in the range of about 0.01–10 weight percent of said support, and in one embodiment, can exist in the range of about 0.1–1 weight percent of said support, and in one further embodiment, can exist in the range of about 0.1–0.5 weight percent of said support. Although any Group IVa metal, when in compound form, is fully within the scope of this invention, some convenient compounds are the halides, nitrates, oxalates, acetates, carbonates, propionates, tartrates, bromates, chlorates, oxides, hydroxides, and the like of tin, germanium and lead. Tin, itself, is the preferred Group IVa metal and impregnation of the support with tin compounds such as the stannous halides is particularly effective and convenient.

Generally speaking, the Group VIII and Group IVa compounds, which can be combined with the supports to form the catalysts used in the dehydrogenation subprocess can be any compound in which all elements, other than those of Group VIII, or Group IVa, are volatilized during calcination. These compounds can be sequentially combined with the support, in any order, or for convenience, can be applied simultaneously in a single impregnation operation. After impregnation, the composite solids are dried and calcined.

The dehydrogenation subprocess is conducted under any suitable operating conditions. Generally, the dehydrogenation is carried out such that the temperature in the inlet portion of the catalyst beds is at a temperature in the range of about 900° F. to about 1,150° F., preferably about 960° F. to about 1,020° F. The dehydrogenation is also conducted at a pressure in the range of about 0 to about 200 psig, preferably about 0 to about 100 psig. Generally, the molar ratio of steam to hydrocarbon is in the range of about 1/1 to about 25/1, preferably about 2/1 to 10/1. The use of an externally heated reactor, i.e., a reactor within a fired furnace, enables one to carry out the present invention with the lower levels of steam. The liquid hourly space velocity of hydrocarbon, i.e., volume of hydrocarbon per volume of catalyst per hour, is generally in the range of about 0.5 to about 10, preferably about 2.0 to about 6.

The regeneration steps can also be conducted under any suitable conditions. Generally the temperature and pressure of the catalyst bed is as in the dehydrogenation step. Oxygen is employed in the steam in an amount in the range of about 0.5 to about 5.0 mole percent, or higher, of the moles of steam.

The hydrocarbon feed to the dehydrogenation process system can be any dehydrogenatable hydrocarbon. The process is particularly suitable for hydrocarbons having from 3 to 8 carbon atoms per molecule. Preferably, the dehydrogenatable hydrocarbons are saturated hydrocarbons and, most preferably, they are isobutane so as to provide an isobutylene feed for charging to an etherification subprocess.

The isobutylene feed produced by the dehydrogenation subprocess is charged or passed to an etherification subprocess whereby the iso-olefins present in feedstream are converted to ethers by reaction with primary or secondary alcohols in the presence of an acid ion exchange resin catalyst. Generally, the iso-olefins include those hydrocarbons having 5 to 16 carbon atoms per molecule. Examples of such iso-olefins include isobutylene, isoamylene, isohexylene, isoheptylene, isooctylene, isononylene, isodecylene, isoundecylene, isododecylene, isotridecylene, isotetradecylene, isopentadecylene, and isohexadecylene, or mixtures of two or more thereof.

The alcohols which may be utilized in the etherification subprocess include the primary and secondary aliphatic alcohols having from 1 to 12 carbon atoms, such as methanol, ethanol, propanol, isopropanol, the primary and secondary butanols, pentanols, hexanols, ethylene glycol, propylene glycol, butylene glycol, the polyglycols and glycerol, etc., or mixtures of two or more thereof.

The presently preferred reactants of the etherification subprocess are methanol and isobutylene and/or an amylene because they respectively yield methyl tertiary butyl ether (MTBE) and tertiary amyl methyl ether (TAME) which have utility as octane improvers for gasoline. Accordingly, it is currently preferred for the iso-olefins to be predominately isobutylene and isoamylene compounds with the double bond on the tertiary carbon atom of said isoamylene compounds and the alcohol predominately methanol. Another preferred embodiment of this invention includes the use of the reactants ethanol and isobutylene to yield ethyl tertiary butyl ether (ETBE).

It is generally preferred for the iso-olefin and the alcohol to be passed through the etherification reaction zone in the presence of diluents which do not have an adverse effect upon the etherification reaction. The diluents can be present in a separate stream, but preferably the diluent is in the iso-olefin stream. Examples of suitable diluents include alkanes and straight chain olefins. The feed to the reactor, excluding alcohol, is generally diluted so as to include about 2 to about 80 weight percent iso-olefin, preferably from about 10 to about 60 weight percent and, more preferably, from 30 to 50 weight percent.

The acid ion-exchange catalysts useful in the etherification subprocess of the present invention are relatively high molecular weight carbonaceous material containing at least one $SO_3H$ functional group. These catalysts are exemplified by the sulfonated coals ("Zeo-Karb H", "Nalcite X" and "Nalcite AX") produced by the treatment of bituminous coals with sulfuric acid and commercially marketed as zeolitic water softeners or base exchangers. These materials are usually available in a neutralized form and in this case must be activated to the hydrogen form by treatment with a strong mineral acid such as hydrochloric acid and water washed to remove sodium and chloride ions prior to use. The sulfonated resin type catalysts are preferred for use in the present invention. These catalysts include the reaction products of phenolformaldehyde resins with sulfuric acid ("Amberlite IR-1", "Amberlite IR-100" and "Nalcite MX"). Also useful are the sulfonated resinous polymers of coumarone-indene with cyclopentadiene, and furfural and sulfonated polymers of cyclopentadiene with furfural. The most preferred cationic exchange resins are strongly acidic exchange resins consisting essentially of sulfonated polystyrene resin, for instance, a divinylbenzene cross-linked polystyrene matrix having from 0.5 to 20 percent and preferably from 4 to 16 percent of copolymerized divinylbenzene therein to which are ionizable or functional nuclear sulfonic acid groups. These resins are manufactured and sold commercially under various trade names such as "Dowex 50", "Nalcite HCR" and "Amberlyst 15". As commercially obtained they have solvent contents of about 50 percent and can be used as is or the solvent can be removed first. The resin particle size is not particularly critical and therefore is chosen in accordance with the manipulative advantages associated with any particular size. Generally mesh sizes of 10 to 50 U.S. Sieve Series are preferred. The reaction may be carried out in either a stirred slurry reactor or in a fixed bed continuous flow reactor. The catalyst concentration in a stirred slurry reactor should be sufficient to provide the desired catalytic effect. Generally catalyst concentration should be 0.5 to 50 percent (dry basis) by weight of the reactor contents with from 1 to 25 percent being the preferred range.

Acid ion exchange resins, such as Rohm & Haas Amberlyst 15 and Dow Chemical Dowex M-31, are currently the most preferred catalysts for the etherification.

The temperature for the etherification reaction zone and the space velocity for the feed to the etherification reaction zone can be selected as desired depending upon the degree of conversion desired and the temperature at which oligomerization becomes a problem. Generally, the temperature of the reaction zones will be in the range of about 86° F. to about 248° F., preferably about 95° F. to about 176° F. Pressures are generally selected to ensure that the charges and the products remain in the liquid phase during the reaction. Typical pressures are in the range of about 30 to about 300 psig. Generally, the liquid hourly space velocity (LHSV) of feed in the reactor will be in the range of about 1 to about 10 $hr^{-1}$, preferably from about 2 to about 8 $hr^{-1}$, and most preferably from 3 to 6 $hr^{-1}$.

The molar ratio of alcohol to iso-olefin in etherification reaction zone feedstream will generally be in the range of about 0.5/1 to about 4/1, preferably about 0.8/1 to about 1.2/1, most preferably about 1/1.

The etherification reactor product stream containing ether, alcohol and hydrocarbon is charged or passed to separation means for separating it into a overhead product, comprising alcohol and hydrocarbon, and as bottoms product, comprising ether. The separation means is preferably a conventional distillation unit which includes a distillation unit which includes a distillation column or fractionator equipped with trays or filled with packing for providing liquid-vapor contact. A general description of distillation operations is provided in *Perry's Chemical Engineers' Handbook, Sixth Edition*, published by McGraw-Hill, Inc., 1984 at pages 13-5 through 13-9, which text is incorporated herein by reference. Mixed with the etherification reactor product stream is a controlled amount of isobutane such as to permit the reduction in the alcohol concentration in the fractionator bottoms product thereby providing a high purity ether product as described elsewhere herein.

The overhead product from etherification reactor product stream fractionator is recycled to the dehydrogenation subprocess by mixing it with an isobutane feed. The resultant mixture is, therefore, charged to the dehydrogenation unit. An additional embodiment of the invention includes passing a portion of the mixture to the fractionator.

Now referring to FIG. 1, there is provided a schematic representation of the process system 10 which includes dehydrogenation system 12, etherification system 14 and fractionator 16. A feedstream containing isobutane is passed to dehydrogenation system 12 through conduit 18. At least a portion of the overhead product containing alcohol and hydrocarbons from fractionator 16 passes by way of conduit 20 and is mixed with the feedstream of conduit 18. The resultant mixture passes through conduit 22 to be charged to dehydrogenation system 12. Dehydrogenation system 12 provide means for dehydrogenating the isobutanes in the feed mixed to thereby produce an isobutylene feed for charging to etherification system 14.

The isobutylene feed passes from dehydrogenation system 12 through conduit 24 to etherification system 14. Etherification system 14 provides for reacting the isobutylene feed with a primary alcohol to thereby provide an etherification reactor effluent stream. Alcohol feed is provided to etherification system by way of conduit 26. The etherification reactor effluent stream passes from etherification system 14 through conduit 28. A portion of the feed containing isobutane can pass by way of conduit 30 and is mixed with the etherification reactor effluent stream prior to charging or passing the thus-formed mixture to fractionator 16.

As an alternative embodiment of the invention, a portion of the mixture of feed containing isobutane and fractionator overhead product passing through conduit 22 can pass through conduits 32 and 34 to be mixed with the etherification reactor effluent stream. Fractionator 16 bottoms product containing ether passes therefrom via conduit 36.

The following calculated example is presented to further illustrate the invention.

EXAMPLE

Presented in Table 1 is a summary of the results from a fractionator simulation for a base case and an inventive case. The base case simulation includes an etherification reaction zone product stream which includes an additional concentration of isobutane above that which would normally be in an etherification reaction zone product stream. The inventive case is a simulation of the fractionation in which 55.6 lb mol per hour of isobutane is added to the base case feed. As can be seen from the difference columns of Table I, the addition of an incremental quantity of isobutane to the fractionator feed stream results in an incremental increase in the methanol and an incremental decrease in the MTBE in the fractionator overhead. Thus, there is a greater recovery of MTBE in the fractionator bottoms which is also a higher purity MTBE product due to the reduction in the alcohol concentration.

TABLE 1

Results of Fractionator Simulation for Base Case versus Inventive Case

| | Base Case | | | Inventive Case | | | Difference between Inventive Case and Base Case | | |
|---|---|---|---|---|---|---|---|---|---|
| Stream No. | 1 | 2 | 3 | 1 | 2 | 3 | 1 | 2 | 3 |
| Stream Name | Feed | Overhead | Bottoms | Feed | Overhead | Bottoms | Feed | Overhead | Bottoms |
| Temp °F. | 175 | 134.55 | 281.49 | 175.00 | 134.30 | 281.99 | | | |
| Pres psia | 125 | 118.00 | 123.00 | 125.00 | 118.00 | 123.00 | | | |
| Enth MMBtu/h | −106.15 | −42.12 | −63.07 | −109.05 | −45.64 | −63.10 | | | |
| Vapor mole fraction | 0.08 | 0.00 | 0.00 | 0.14 | 0.00 | 0.00 | | | |
| Total lbmol/h | 1176.39 | 685.39 | 491.00 | 1232.01 | 741.00 | 491.00 | 55.62 | 55.61 | 0 |
| Flowrates in lbmol/h | | | | | | | | | |
| Propylene | 0.28 | 0.28 | 0.00 | 0.28 | 0.28 | 0.00 | 0 | 0 | 0 |
| Propane | 1.78 | 1.78 | 0.00 | 1.78 | 1.78 | 0.00 | 0 | 0 | 0 |
| I-Butene | 34.07 | 34.07 | 0.00 | 34.07 | 34.07 | 0.00 | 0 | 0 | 0 |
| I-Butane | 556.19 | 556.19 | 0.00 | 611.81 | 611.81 | 0.00 | 55.62 | 55.62 | 0 |
| N-Butane | 24.12 | 24.12 | 0.00 | 24.12 | 24.12 | 0.00 | 0 | 0 | 0 |
| 1-Butene | 8.58 | 8.58 | 0.00 | 8.58 | 8.58 | 0.00 | 0 | 0 | 0 |
| Trans-2-Butene | 10.98 | 10.98 | 0.00 | 10.98 | 10.98 | 0.00 | 0 | 0 | 0 |
| Cis-2-Butene | 7.56 | 7.56 | 0.00 | 7.56 | 7.56 | 0.00 | 0 | 0 | 0 |
| 1,3-Butadiene | 1.00 | 1.00 | 0.00 | 1.00 | 1.00 | 0.00 | 0 | 0 | 0 |
| N-Hexane | 0.52 | 0.00 | 0.52 | 0.52 | 0.00 | 0.52 | 0 | 0 | 0 |
| Dimethyl Ether | 0.52 | 0.52 | 0.00 | 0.52 | 0.52 | 0.00 | 0 | 0 | 0 |
| Methanol | 39.90 | 36.78 | 3.12 | 39.90 | 38.10 | 1.80 | 0 | 1.32 | <1.32> |
| Tert-Butanol | 2.24 | 0.00 | 2.24 | 2.24 | 0.00 | 2.24 | 0 | 0 | 0 |
| 2-Diisobutylene | 1.33 | 0.00 | 1.33 | 1.33 | 0.00 | 1.33 | 0 | 0 | 0 |
| MTBE | 485.08 | 1.36 | 483.72 | 485.08 | 0.00 | 485.08 | 0 | <1.36> | 1.36 |
| Water | 2.24 | 2.16 | 0.08 | 2.24 | 2.21 | 0.03 | 0 | 0.04 | <0.04> |

Reasonable variations and modifications are possible within the scope of the foregoing disclosure, drawings and appended claims.

That which is claimed is:

1. A method for fractionating an etherification reaction zone product stream containing ether, alcohol and hydrocarbons so as to provide a high purity ether product and an overhead product, said method comprises the steps of:

mixing a controlled amount of isobutane with said etherification reaction zone product stream to form a mixed stream; and fractionating said mixed stream into said high purity ether product and said overhead product;

wherein said controlled amount of isobutane is such as to permit the reduction of an alcohol concentration in said high purity ether product below a desired concentration.

2. A method as recited in claim 1 wherein said desired concentration is less than about 1.5 mol percent.

3. A method as recited in claim 1 wherein said controlled amount of isobutane mixed with said etherification reaction zone product stream is in the range upwardly to about 4 mols isobutane added per tool ether in said etherification reaction zone product stream.

4. A method as recited in claim 1 wherein the concentration of alcohol in said etherification reaction zone product stream is in the range from about 1 to about 20 mol percent.

5. A process comprising:

passing a feed comprising isobutane to a dehydrogenation process system for dehydrogenating the isobutane in said feed and to thereby provide an isobutylene feed;

passing said isobutylene feed to an etherification process system for reacting the isobutylene of said isobutylene feed with an alcohol to thereby provide an etherification reaction zone product stream comprising ether and alcohol;

mixing isobutane with said etherification reaction zone product stream to form a mixed stream;

passing said mixed stream to a fractionator whereby said mixed stream is separated into a bottoms product comprising ether and an overhead product comprising isobutane and alcohol; and mixing said overhead product with said feed.

6. A method as recited in claim 5 wherein the concentration of alcohol in said bottoms product is less than about 1.5 mol percent.

7. A method as recited in claim 5 wherein the amount of isobutane mixed with said etherification reaction zone product stream is in the range upwardly to about 4 mols isobutane per mole ether in said etherification reaction zone product stream.

8. A method as recited in claim 5 wherein the concentration of alcohol in said etherification reaction zone product stream is in the range of from about 1 to about 20 mol percent.

9. A process comprising:

passing a dehydrogenation feed comprising isobutane to a dehydrogenation process system for dehydrogenating the isobutane in said feed to thereby provide an isobutylene feed;

passing said isobutylene feed to an etherification process system for reacting the isobutylene of said isobutylene feed with an alcohol and to thereby provide an etherification reaction zone product stream comprising ether and alcohol; and mixing a portion of said dehydrogenation feed with said etherification reaction zone product stream to form a mixed stream;

passing said mixed stream to a fractionator whereby said mixed stream is separated into a bottoms product comprising ether and an overhead product comprising isobutane and alcohol; and mixing said overhead product with isobutane to thereby form said dehydrogenation feed.

10. A method as recited in claim 9 wherein the concentration of alcohol in said bottoms product is less than about 1.5 mol percent.

11. A method as recited in claim 9 wherein the amount of dehydrogenation feed mixed with said etherification reaction zone product stream is such as to provide an alcohol concentration in said mixed stream of less than about 5 mol percent.

12. A method as recited in claim 9 wherein the concentration of alcohol in said etherification reaction zone product stream is in the range of from about 1 to about 20 mol percent.

* * * * *